US005785822A

United States Patent [19]

Cerri et al.

[11] Patent Number: 5,785,822
[45] Date of Patent: Jul. 28, 1998

[54] PROCESS FOR SEPARATING DIFLUOROMETHANE

[75] Inventors: Gustavo Cerri, Boonton, N.J.; Kin Ching Kong, Woodside; Charles Francis Swain, Williamsville, both of N.Y.; Rajat Subhra Basu, East Amherst, N.Y.

[73] Assignee: AlliedSignal Inc., Morristown, N.J.

[21] Appl. No.: 652,891

[22] Filed: May 23, 1996

[51] Int. Cl.$^6$ .................................................. B01D 3/34
[52] U.S. Cl. ......................... 203/67; 203/80; 570/170; 570/178
[58] Field of Search .................. 203/67, 80; 570/170, 570/178

[56] References Cited

U.S. PATENT DOCUMENTS

| 5,211,020 | 5/1993 | Taylor et al. | 62/11 |
| 5,470,442 | 11/1995 | Mahler et al. | 203/56 |
| 5,523,015 | 6/1996 | Daikin et al. | 252/171 |

*Primary Examiner*—Nina Bhat
*Attorney, Agent, or Firm*—Lois A. Gianneschi

[57] ABSTRACT

The present invention provides a method for separating dichlorodifluoromethane from difluoromethane. More specifically, a process is provided for separating dichlorodifluoromethane and difluoromethane using azeotropic distillation.

22 Claims, No Drawings

PROCESS FOR SEPARATING DIFLUOROMETHANE

FIELD OF THE INVENTION

The present invention relates to a method for separating dichlorodifluoromethane ("CFC-12") from difluoromethane ("HFC-32"). More specifically, a process is provided for separating CFC-12 from HFC-32 using azeotropic distillation.

BACKGROUND OF THE INVENTION

A number of processes for the production of HFC-32, are known. The products of these processes contain reaction by-products including CFC-12. It is desirable to remove these reaction by-products in order to provide HFC-32 product.

However, some reaction byproducts, such as CFC-12, form azeotropic mixtures with HFC-32 making their separation difficult by conventional methods. Therefore a need exists for an efficient and effective method for separating CFC-12 from HFC-32.

DESCRIPTION OF THE INVENTION AND THE PREFERRED EMBODIMENTS

The invention provides a method for separating CFC-12 from a mixture of HFC-32 and CFC-12. It has been discovered that HFC-32 and CFC-12 form a low-boiling, azeotrope having a weight percent ratio of HFC-32 to CFC-12 of about 71 to 29 at atmospheric pressure and a normal boiling point of −65±1° F. The weight percent ratio of this azeotrope varies with pressure, the ratio being about 79 to 21 at 300 psig and a boiling point of 93±1° F.

Because the boiling points of pure CFC-12 and HFC-32 are −21.6° F. and −61° F., respectively, CFC-12 would be expected to be removed as the residue, or bottoms product, in a distillation of a CFC-12 and HFC-32 mixture. The process of the invention is based on the discovery that it is possible to use the HFC-32/CFC-12 azeotrope to separate CFC-12 in the column distillate in a distillation of a HFC-32/CFC-12 mixture in which mixture the CFC-12 content is less than the amount needed to form the HFC-32/CFC-12 azeotrope.

By column distillate, for purposes of this invention, is meant the overhead distillate for continuous operations or a distillate cut in a batch operation. By azeotrope is meant a mixture that is a constant boiling mixture of two or more components, the vapor composition and liquid composition of which are equal at thermodynamic state pressure and temperature. In other words, the composition of the vapor formed during partial boiling or evaporation of an azeotrope is identical to the mixture's liquid composition.

The invention provides a method for separating CFC-12 from a mixture of CFC-12 and HFC-32. The process of the invention comprises the steps of: (A) distilling a mixture comprising HFC-32 and an amount of CFC-12 that is less than that of a HFC-32/CFC-12 azeotropic mixture by passing the mixture through a distillation apparatus in order to separate CFC-12 as a HFC-32/CFC-12 azeotrope in the column distillate and to produce a HFC-32 bottoms product, which product has a reduced level of CFC-12 compared to the HFC-32/CFC-12 mixture distilled; and (B) collecting the HFC-32 bottoms product from the distillation column.

This invention uses an azeotrope of CFC-12 and HFC-32 as a reflux stream in a distillation to reduce the CFC-12 level of a mixture of HFC-32 and CFC-12, in which mixture the CFC-12 content is less than the that of the HFC-32/CFC-12 azeotrope. In step (A) of the process of this invention, a mixture containing HFC-32 and an amount of CFC-12 less than that of the HFC-32/CFC-12 azeotrope is distilled by passing the mixture through a distillation apparatus. Any type of distillation apparatus, such as a column with trays or a packed column, may be used in the process of the invention. Further, distillation may be performed as a continuous or batch operation.

The HFC-32 and CFC-12 mixture may be produced by the liquid or vapor phase reaction of methylene chloride ("HCC-30") or chlorofluoromethane ("HCFC-31") with hydrogen fluoride or the hydrogenation of CFC-12. The HFC-32/CFC-12 mixture may be crude reactor effluent containing unreacted starting materials, reaction intermediates, and byproducts. Thus, it will be recognized by one ordinarily skilled in the art that the HFC-32/CFC-12 mixture may contain components such as, without limitation, HCC-30, hydrogen fluoride, trifluoromethane ("HFC-23"), chlorodifluoromethane ("HCFC-22"), and hydrogen chloride. Alternatively, the HFC-32/CFC-12 mixture may be treated reactor effluent. By treated reactor effluent is meant effluent that has been treated by any of the convenient methods such as distillation, water or caustic scrubbing, drying, and the like, or combinations thereof in order to remove the unreacted starting materials, reaction intermediates, and byproducts.

Distilling the HFC-32/CFC-12 mixture by passing it through the distillation apparatus provides for the removal of CFC-12 as the HFC-32/CFC-12 azeotrope in the column distillate. The column distillate may contain other low boiling components present in the mixture. For example, depending on the number of stages or the distillation apparatus and the reflux ratio used, an additional amount of HFC-32 beyond that of the azeotropic ratio of HFC-32/CFC-12 may be present in the column distillate.

In a continuous distillation, the CFC-12 may be removed from the top of the column along with the azeotropic HFC-32. In a batch distillation, the CFC-12 may be removed in a distillate cut, along with azeotropic HFC-32. As indicated, the column distillate may also contain other low boiling components from the starting mixture as well as an excess of HFC-32 beyond the azeotropic amount.

The temperature at which the distillation is carried out is readily determinable by one ordinarily skilled in the art. The distillation may be carried out at pressures of up to about 500 psia. Higher pressures are advantageous in that reflux may be produced with a higher temperature cooling medium which is less costly per unit of cooling. However, distillation at higher pressures can be more difficult because the relative volatility of the azeotrope and the HFC-32 and CFC-12 content of the azeotrope decrease with increasing pressure, requiring a higher reflux ratio and/or more stages of separation. Therefore, preferably, distillation is carried out at a pressure from about 75 psia to about 200 psia.

The distillation of step (A) produces a HFC-32 bottoms product, which product has a reduced level of CFC-12 compared to the HFC-32/CFC-12 mixture distilled. In step (B), the HFC-32 bottoms product is collected, which collection may be carried out by any convenient means. The HFC-32 bottoms product may also contain other high boiling components present in the original mixture. In a batch distillation, the HFC-32 product is collected in a distillate cut subsequent to the CFC-12 cut or in the material remaining in the bottoms of the batch still. In a continuous distillation, the HFC-32 product may be removed from the distillation apparatus as the bottoms product.

It has been discovered that the amount of HFC-32 that can be recovered in step (B) will depend on the amount of CFC-12 in the HFC-32/CFC-12 mixture. With a CFC-12 concentration of greater than about 10 weight percent, the fraction HFC-32 in the mixture that can be collected in step (B) decreases significantly. Preferably, the CFC-12 content of the HFC-32/CFC-12 mixture is about 10 weight percent or less.

In cases in which the CFC-12 content of the HFC-32/CFC-12 mixture exceeds this amount, a portion of the HFC-32 in the column distillate of step (A) may be recovered by passing the column distillate over a catalyst to convert CFC-12 into products that are more easily separated from HFC-32. Therefore, in another embodiment of the invention, in a step (C), the column distillate is contacted with a catalyst in order to form a product mixture. Suitable catalysts include ferric chloride and chromium oxyfluoride. By contacting the CFC-12 with such catalysts at a temperature greater than about 400° C., at least a portion of the CFC-12 converts to a product. The product may be chlorotrifluoromethane ("CFC-13") and/or trichlorofluoromethane ("CFC-11"). If hydrogen fluoride is also present, the CFC-12 will convert mainly to CFC-13. In step (D), the product mixture is distilled to remove the CFC-11 and/or CFC-13 as the bottoms product and a purified HFC-32/CFC-12 mixture as column distillate. In a step (E), the purified HFC-32/CFC-12 mixture is then recycled to step (A).

In yet another embodiment of the invention, a process for producing purified HFC-32 is provided. In step (A) of this embodiment, a mixture comprising HFC-32 and an amount of CFC-12 less than that of a HFC-32/CFC-12 azeotrope, which mixture is a treated reactor effluent, is distilled in a first distillation column in order to separate CFC-12 as the HFC-32/CFC-12 azeotrope in the column distillate and to produce a HFC-32 bottoms product. The HFC-32 bottoms product has a reduced level of CFC-12 compared to the starting material. In step (B), the HFC-32 product is distilled in a second distillation in order to remove impurities and recover purified HFC-32.

The invention will be clarified further by a consideration of the following examples that are intended to be purely exemplary.

EXAMPLES

Example 1

A mixture containing 98.2 wt percent HFC-32, 0.4 wt percent CFC-12, and 1.4 wt percent other byproducts, such as HFC-23, HCFC-22 and HCC-30, from the reaction of HCC-30 with HF was charged to a batch distillation column. After operating the column on total reflux for 8 hours, a sample of the distillate was analyzed and then three separate distillate products were collected in succession. The three samples were analyzed by gas chromatography as was a sample of the remaining material in the reboiler. The analysis results are provided on Table I.

TABLE I

| Component | Total Reflux Sample | Lights Cut | Main Cut | Product | Reboiler Contents |
|---|---|---|---|---|---|
| HFC-32 | 81.6 wt % | 88.9 wt % | 99.9 wt % | 99.99 wt % | 89.8 wt % |
| CFC-12 | 8.3 wt % | 4.5 wt % | 0.08 wt % | ND | ND |
| Other | 10.1 wt % | 6.6 wt % | 0.02 wt % | 0.01 wt % | 10.2 wt % |

ND denotes that component was not detectable.

As can be seen from the data on Table I, the CFC-12 was separated from the HFC-32 and concentrated in the overhead distillate of the batch distillation column as the low boiling azeotrope of HFC-32. As a result, most of the CFC-12 was removed in the first distillate cut, the lights cut. The distillation was continued to recover the HFC-32 from the high boiling components in the original mixture (30, 31, 22 etc.) yielding two additional distillate cuts, the main cut and the third cut, which cuts had a reduced CFC-12 content when compared to the original mixture.

Examples 2–13

Vapor-liquid equilibrium ("VLE") data were determined from the laboratory analysis of the vapor and liquid composition of the mixtures of these two components at different temperatures and pressures. The data were then fitted using the Universal Quasi-Chemical Functional Group Activity Coefficient ("UNIFAC") as the model to represent the VLE data for the mixture. The UNIFAC model was then used in computer simulations to demonstrate the separation that can be achieved in a distillation column using a mixture containing only HFC-32 and CFC-12. The results of the calculations are provided in Tables II through V. The simulations showed that a large portion of the CFC-12 can be removed in the overhead distillate to produce a bottoms product HFC-32 that has a reduced CFC-12 content. The CFC-12 remaining in the HFC-32 bottoms product was reduced significantly, or to less than 500 ppm CFC-12.

TABLE II

| | Example 2 | Example 3 | Example 4 |
|---|---|---|---|
| CFC-12 Feed (ppm) | 50,000 | 50,000 | 50,000 |
| Number of Ideal Stages | 20 | 20 | 20 |
| Reflux Ratio | 38 | 73 | 107 |
| Reflux: Column Feed | 8.7 | 16.5 | 24.4 |
| HFC-32 Recovered in Bottoms (% Feed HFC-32) | 79 | 79 | 79 |
| CFC-12 in Bottoms (ppm) | 487 | 252 | 189 |

TABLE III

| | Example 5 | Example 6 | Example 7 |
|---|---|---|---|
| CFC-12 Feed (ppm) | 10,000 | 10,000 | 10,000 |
| Number Ideal Stages | 20 | 20 | 20 |
| Reflux Ratio | 194 | 367 | 539 |
| Reflux: Column Feed | 8.7 | 16.5 | 24.1 |
| HFC-32 Recovered in Bottoms (% Feed HFC-32) | 96 | 96 | 96 |
| CFC-12 in Bottoms (ppm) | 264 | 164 | 138 |

TABLE IV

| | Example 8 | Example 9 | Example 10 |
|---|---|---|---|
| CFC-12 Feed (ppm) | 2,000 | 2,000 | 2,000 |
| Number Ideal Stages | 20 | 20 | 20 |
| Reflux Ratio | 969 | 1828 | 2687 |
| Reflux: Column Feed | 8.7 | 16.3 | 24.0 |
| HFC-32 Recovered in Bottoms (% Feed HFC-32) | 99 | 99 | 99 |
| CFC-12 in Bottoms (ppm) | 163 | 117 | 89 |

TABLE V

|  | Example 11 | Example 12 | Example 13 |
| --- | --- | --- | --- |
| CFC-12 Feed (ppm) | 1,000 | 1,000 | 1,000 |
| Number Ideal Stages | 20 | 20 | 20 |
| Reflux Ratio | 1929 | 3640 | 5361 |
| Reflux: Column Feed | 8.7 | 16.3 | 24.0 |
| HFC-32 Recovered in Bottoms (% Feed HFC-32) | 99.6 | 99.6 | 99.6 |
| CFC-12 in Bottoms (ppm) | 129 | 96 | 77 |

Example 14

In this example, the UNIFAC model was used to calculate the separation of a HFC-32/CFC-12 mixture containing products, byproducts, reaction intermediates, and unreacted starting material from the reaction of HCC-30 with hydrogen fluoride to produce HFC-32. Removal of CFC-12 along with the lower boiling components, HCl, HFC-23, and an amount of HFC-32 equal to or greater than the HFC-32/CFC-12 azeotropic mixture. The bottoms product from this distillation had a much reduced concentration of CFC-12 as a percentage of the HFC-32 in the stream and also contains higher boiling components, HF, HCC-30, HCFC-22, from the reaction product. The bottoms product from the distillation may be sent to further processing to produce an essentially pure HFC-32 product suitable for commercial use. Table VI illustrates the reaction product composition along with the distillate and bottoms product and the reflux ratio and ideal stages of the distillation.

TABLE VI

| Example 14 | Feed (lb/hr) | Distillate (lb/hr) | Bottoms (lb/hr) |
| --- | --- | --- | --- |
| HCl | 140.1 | 140.1 | — |
| HFC-23 | 0.1 | 0.1 | — |
| HFC-32 | 99.8 | 11.8 | 88.0 |
| HCFC-22 | 0.2 | — | 0.2 |
| CFC-12 | 0.2 | 0.15 | 0.05 |
| HCFC-31 | 5.0 | — | 5.0 |
| Methylene Chloride | 40.8 | — | 40.8 |
| HF | 153.5 | — | 153.5 |
| Reflux Ratio | — | 146.7 | — |
| Stages(ideal) | — | 30 | — |

Example 14 demonstrates the use of the invention to reduce the CFC-12 content of a mixture produced from the reaction of methylene chloride and hydrogen fluoride.

What is claimed is:

1. A process for separating dichlorodifluoromethane from a mixture of dichlorodifluoromethane and difluoromethane comprising the steps of:

(A) distilling a mixture comprising dichlorodifluoromethane and difluoromethane, the mixture having a weight percent ratio of difluoromethane to dichlorodifluoromethane less than the weight percent ratio of a dichlorodifluoromethane/difluoromethane azeotrope, by passing the mixture through a distillation apparatus in order to separate dichlorodifluoromethane in a column distillate having a dichlorodifluoromethane/difluoromethane weight percent ratio at least equal to the azeotropic ratio and greater than the weight percent ratio of the mixture distilled and to produce a difluoromethane bottoms product having a reduced content of dichlorodifluoromethane compared to the difluoromethane/dichlorodifluoromethane mixture distilled; and (B) collecting the difluoromethane bottoms product from the distillation column.

2. The process of claim 1 wherein the mixture of dichlorodifluoromethane and difluoromethane is a crude reactor effluent produced by a reaction of methylene chloride and hydrogen fluoride.

3. The process of claim 2 wherein the reaction is a vapor phase reaction.

4. The process of claim 2 wherein the reaction is a liquid phase reaction.

5. The process of claim 1 wherein the mixture of dichlorodifluoromethane and difluoromethane is a crude reactor effluent produced by a reaction of chlorofluoromethane and hydrogen fluoride.

6. The process of claim 5 wherein the reaction is a vapor phase reaction.

7. The process of claim 5 wherein the reaction is a liquid phase reaction.

8. The process of claim 1 wherein the mixture of dichlorodifluoromethane and difluoromethane is a crude reactor effluent produced by a hydrogenation reaction of dichlorodifluoromethane.

9. The process of claim 1 wherein the mixture of dichlorodifluoromethane and difluoromethane is a treated reactor effluent produced by a reaction of methylene chloride and hydrogen fluoride.

10. The process of claim 9 wherein the reaction is a vapor phase reaction.

11. The process of claim 9 wherein the reaction is a liquid phase reaction.

12. The process of claim 9 in which step (B) comprises distilling the HFC-32 bottoms product in a second distillation in order to remove impurities and recover purified HFC-32.

13. The process of claim 1 wherein the mixture of dichlorodifluoromethane and difluoromethane is a treated reactor effluent produced by a reaction of chlorofluoromethane and hydrogen fluoride.

14. The process of claim 13 wherein the reaction is a vapor phase reaction.

15. The process of claim 13 wherein the reaction is a liquid phase reaction.

16. The process of claim 13 in which step (B) comprises distilling the HFC-32 bottoms product in a second distillation in order to remove impurities and recover purified HFC-32.

17. The process of claim 1 wherein the mixture of dichlorodifluoromethane and difluoromethane is a treated reactor effluent produced by a hydrogenation reaction of dichlorodifluoromethane.

18. The process of claim 1 wherein the dichlorodifluoromethane and difluoromethane mixture has a dichlorodifluoromethane content of about 10 weight percent or less.

19. The process of claim 1 wherein the dichlorodifluoromethane and difluoromethane mixture has a dichlorodifluoromethane content of greater than about 10 weight percent and wherein the process further comprises the steps of:

(C) contacting the column distillate with a catalyst at a temperature of greater than about 400° C. in order to convert at least a portion of the dichlorodifluoromethane into a product and form a product mixture;

(D) distilling the product mixture to remove the product as a bottoms product and a purified difluoromethane/dichlorodifluoromethane mixture as a column distillate; and (E) recycling the purified difluoromethane/ dichlorodifluoromethane mixture to step (A).

20. An azeotropic mixture consisting essentially of difluoromethane and dichlorodifluoromethane in a weight percent ratio of from about 71 to about 29 at atmospheric pressure and a normal boiling point of −65±1° F.

21. The azeotropic mixture of claim 20 wherein the weight percent of difluoromethane to dichlorodifluoromethane varies from about 71 to about 29 at atmospheric pressure to about 79 to about 21 at 300 psig.

22. An azeotropic mixture consisting essentially of difluoromethane and dichlorodifluoromethane in a weight percent ratio of from about 79 to about 21 at 300 psig and a boiling point of 93±1° F.

\* \* \* \* \*